United States Patent [19]

Wu

[11] Patent Number: 5,264,642
[45] Date of Patent: Nov. 23, 1993

[54] MOLECULAR WEIGHT CONTROL OF OLEFIN OLIGOMERS

[75] Inventor: Margaret M. Wu, Skillman, N.J.

[73] Assignee: Mobil Oil Corp., Fairfax, Va.

[21] Appl. No.: 901,282

[22] Filed: Jun. 19, 1992

[51] Int. Cl.$^5$ .............................................. C07C 2/02
[52] U.S. Cl. .................... 585/530; 585/520; 585/10; 585/12; 585/17
[58] Field of Search ............... 585/10, 12, 17, 520, 585/530

[56] References Cited

U.S. PATENT DOCUMENTS

| | | | |
|---|---|---|---|
| 4,827,064 | 5/1989 | Wu | 585/530 |
| 4,827,073 | 5/1989 | Wu | 585/530 |
| 4,879,425 | 11/1989 | Kukes et al. | 585/530 |

OTHER PUBLICATIONS

Weiss, et al, Journal Of Catalysis, 88,424-430, Polymerization of 1-alkenes with Chromium II; 1984.

*Primary Examiner*—Patrick P. Garvin
*Assistant Examiner*—E. D. Irzinski
*Attorney, Agent, or Firm*—Alexander J. McKillop; Malcolm D. Keen

[57] ABSTRACT

A process is disclosed to produce liquid oligomers of olefins, such as 1-decene, with controlled molecular weight and with branch ratios below 0.19 and having higher viscosity indices than oligomers with higher branch ratios. These oligomers with low branch ratios and controlled molecular weight can be used as basestocks for many lubricants or greases with an improved viscosity-temperature relationship, oxidative stability, volatility, etc. They can also be used to improve viscosities and viscosity indices of lower quality oils. The olefins can, for example, be oligomerized in the presence of hydrogen over a supported and reduced metal oxide catalyst from Group VIB of the Periodic Table to give oligomers of controlled viscosity suitable for lubricant application. More particularly, the instant invention is directed to a process for the oligomerization of olefinic hydrocarbons containing 6 to 20 carbon atoms which comprises oligomerizing said hydrocarbon in the presence of hydrogen under oligomerization conditions, wherein the reaction product consists essentially of substantially non-isomerized olefins. For example, alpha olefins such as 1-decene, and wherein a major proportion of the double bonds of the olefins or olefinic hydrocarbons are not isomerized, in the presence of a suitable catalyst, e.g., a supported and reduced metal oxide catalyst from Group VIB of the Periodic Table.

25 Claims, No Drawings

MOLECULAR WEIGHT CONTROL OF OLEFIN OLIGOMERS

This application relates to a process for the production from alpha olefins of oligomers with low branch ratios and controlled molecular weight which can be used as basestocks for lubricants or grease providing improved viscosity-temperature relationship, oxidative stability, volatility, or to improve lower quality oils.

BACKGROUND OF THE INVENTION

Catalytic oligomerization of olefins is a known technique for manufacturing hydrocarbon basestocks useful as lubricants. Efforts to improve upon the performance of natural mineral oil based lubricants by the synthesis of oligomeric hydrocarbon fluids have been the subject of important research and development in the petroleum industry for several decades, leading to recent commercial production of a number of superior poly(alpha-olefin) synthetic lubricants, hereafter called "PAO". These materials are primarily based on the oligomerization of alpha-olefins (1-alkenes), such as $C_6$–$C_{20}$ olefins. Industrial research effort on synthetic lubricants has generally focused on fluids exhibiting useful viscosities over a wide range of temperature, i.e., improved viscosity index (VI), while also showing lubricity, thermal and oxidative stability and pour point equal to or better than mineral oil. These newer synthetic lubricants provide lower friction and hence increase mechanical efficiency across the full spectrum of mechanical loads and do so over a wider range of operating conditions than mineral oil lubricants.

Well known structural and physical property relationships for high polymers as contained in the various disciplines of polymer chemistry have pointed the way to 1-alkenes as a fruitful field of investigation for the synthesis of oligomers with the structure thought to be needed to confer improved lubricant properties thereon. Due largely to studies on the polymerization of propene and vinyl monomers, the mechanism of the polymerization of 1-alkene and the effect of that mechanism on polymer structure is reasonably well understood, providing a strong resource for targeting on potentially useful oligomerization methods and oligomer structures. Building on that resource, in the prior art oligomers of 1-alkenes from $C_6$ to $C_{20}$ have been prepared with commercially useful synthetic lubricants from 1-decene oligomerization yielding a distinctly superior lubricant product via either cationic or Ziegler catalyzed polymerization.

One characteristic of the molecular structure of 1-alkene oligomers that has been found to correlate very well with improved lubricant properties in commercial synthetic lubricants is the ratio of methyl to methylene groups in the oligomer. The ratio is called the branch ratio and is calculated from infra red data as discussed in "Standard Hydrocarbons of High Molecular Weight", *Analytical Chemistry*, Vol. 25, no. 10, p.1466 (1953). Viscosity index has been found to increase with lower branch ratio. Prior, oligomeric liquid lubricants exhibiting very low branch ratios have not been synthesized from 1-alkenes. For instance, oligomers prepared from 1-decene by either cationic polymerization have branch ratios of greater than 0.20. Explanations for the apparently limiting value for branch ratio based on a cationic polymerization reaction mechanism involves rearrangement to produce branching. Other explanations suggest isomerization of the olefinic group in the one position to produce an internal olefin as the cause for branching. Whether by rearrangement, isomerization or other mechanism, 1-alkene oligomerization to produce synthetic lubricants as produces excessive branching and constrains the lubricant properties, particularly with respect to viscosity index.

U.S. Pat. No. 4,282,392 to Cupples et al. discloses an alpha-olefin oligomer synthetic lubricant having an improved viscosity-volatility relationship and containing a high proportion of tetramer and pentamer via a hydrogenation process that effects skeletal rearrangement and isomeric composition. The product is a trimer to tetramer ratio no greater than 1:1.

A process using coordination catalysts to prepare high polymers from 1-alkenes, especially chromium catalyst on a silica support, is described by Weiss et al. in Jour. Catalysis 88, 424–430 (1984) and in Offen. DE 3,427,319. The process and products therefrom are discussed in more detail hereinafter in comparison with the process and products of the present process.

It is well known that Lewis acids such as promoted $BF_3$ and/or metal halides can catalyze Friedel-Crafts type reactions. However, olefin oligomers and more particularly PAO oligomers have been produced by methods in which double bond isomerization of the starting 1-olefin occurs easily. As a result, the olefin oligomers have more short side branches. These side branches degrade their lubricating properties.

A significant problem in the manufacture of synthetic lubricants is the production of lubes in a preferred viscosity range in good yield without excessive catalyst deactivation. Frequently, it is difficult to directly produce lower viscosity range lube without incurring lower yields due to the production of non-lube range materials. Methods to control molecular weight of lubes in the oligomerization step are sought after in the art to overcome the problems in the manufacture of, particularly, lower viscosity lubes.

SUMMARY OF THE INVENTION

A new process has now been discovered to produce liquid oligomers of olefins, such as 1-decene, with controlled molecular weight and with branch ratios below 0.19 and having higher viscosity indices than oligomers with higher branch ratios. These oligomers with low branch ratios and controlled molecular weight can be used as basestocks for many lubricants or greases with an improved viscosity-temperature relationship, oxidative stability, volatility, etc. They can also be used to improve viscosities and viscosity indices of lower quality oils. The olefins can, for example, be oligomerized in the presence of hydrogen over a supported and reduced metal oxide catalyst from Group VIB of the Periodic Table to give oligomers suitable for lubricant application. More particularly, the instant application is directed to a process for the oligomerization of olefinic hydrocarbons containing 6 to 20 carbon atoms which comprises oligomerizing said hydrocarbon in the presence of hydrogen under oligomerization conditions, wherein the reaction product consists essentially of substantially non-isomerized olefins. For example, alpha olefins such as 1-decene, and wherein a major proportion of the double bonds of the olefins or olefinic hydrocarbons are not isomerized, in the presence of a suitable catalyst, e.g., a supported and reduced metal oxide catalyst from Group VIB of the Periodic Table.

The use of reduced Group VIB chromium-containing metal oxide on an inert support in the presence of hydrogen oligomerizes liquid olefins with controlled molecular weight. The oligomers are suitable for use as good quality lube oils. It is therefore an object of this invention to oligomerize olefins or mixtures of olefins over a supported and reduced Group VIB metal oxide catalyst in the presence of hydrogen without hydrogenating starting olefins or product polyalphaolefins to obtain lubricants of good quality with controlled molecular weight and viscosity.

These and other objects and features of the invention will be understood from the following detailed description.

DETAIL DESCRIPTION OF THE INVENTION

HVI-PAO oligomers following the oligomerizations step contain olefinic unsaturation. However, in the following description, unless otherwise stated, all references to HVI-PAO oligomers or lubricants for actual use refer to hydrogenated oligomers and lubricants in keeping with the practice of those skilled in the art of lubricant production. Also, examples employed give parts by weight and metric units unless otherwise stated.

Synthesis methods have been found for preparing liquid hydrocarbon lubricant compositions from $C_6$–$C_{20}$ 1-alkene oligomerization that exhibit surprisingly high viscosity index (VI), while exhibiting very low pour point temperature. The product compositions comprise $C_{30}$–$C_{1300}$ hydrocarbons having a branch ratio of less than 0.19; number average molecular weight between 420 and 18,000; weight average molecular weight upto about 45,000; molecular weight distribution between 1 and 5 and pour point below $-15°$ C.

The process has been discovered to produce a 1-decene trimer, 11-octyldocosane, and other unique structures. This compound has been found to exhibit superior lubricant properties either alone or in a mixture with 9-methyl,11-octylheneicosane. Surprisingly, the $C_{30}+$ mixture has a viscosity index of greater than 130 while maintaining a pour point less than $-15°$ C. These products are representative of the present process, usually comprising $C_{30}H_{62}$ alkanes having a branch ratio, or $CH_3/CH_2$ ratio, of less than 0.19. These low branch ratios and pour points characterize the products of the inventive process, referred to herein as high viscosity index polyalpha-olefin or HVI-PAO, conferring upon the compositions especially high viscosity indices in comparison to commercially available polyalpha-olefin (PAO) synthetic lubricants.

These compositions can be prepared by the oligomerization of alpha-olefins such as 1-decene under oligomerization conditions in contact with a supported and reduced valence state metal oxide catalyst from Group VIB of the IUPAC Periodic Table. Chromium oxide is the preferred metal oxide.

As oligomerized, HVI-PAO oligomers are mixtures of dialkyl vinyledenic and 1,2 dialkyl mono-olefins. Lower molecular weight unsaturated oligomers are preferably hydrogenated to produce thermally stable, useful lubricants. Higher molecular weight unsaturated HVI-PAO oligomers are sufficiently thermally stable to be utilized without hydrogenation, and optionally, may be so employed. Both unsaturated and hydrogenated HVI-PAO of lower or higher molecular exhibit viscosity indices of at least 130 and pour point below $-15°$ C.

It has been found that the process described herein to produce the novel HVI-PAO oligomers can be controlled in the presence of hydrogen to yield a high yield of oligomers having weight average molecular weight between about 420 and 45,000, with a preferred number average molecular weight between 420 and 18,000. The yield may be as low as 50°-70% of $C_{30}+$ product having viscosity below 10 cS (100° C.); however, the higher molecular weight products having a viscosity greater than 15 cS may be produced at 85%+ yield.

Measured in carbon numbers, molecular structures generally range from $C_{30}$ to $C_{1300}$. Molecular weight distributions, defined as the ratio of weight averaged molecular to number averaged molecular weight, range from 1 to 5, with a preferred range of 1.01 to 3. Compared to conventional PAO derived from $BF_3$ or $AlCl_3$ catalyzed polymerization of 1-alkene, HVI-PAO of the present invention has been found to have a higher proportion of higher molecular weight polymer molecules in the product.

Viscosities of the novel HVI-PAO oligomers measured at 100° C. range from about 3 cS to 750 cS (centistokes). In the instant invention it has been found that these viscosities can be controlled by incorporating hydrogen in the oligomerization step. The viscosity index for these polyalpha-olefins is approximately described by the following equation:

$$VI = 129.8 + 4.58 \times (V_{100°\,C.})^{0.5},$$

where $V_{100°}$ C. is kinematic viscosity in centistokes.

The oligomer compositions define their unique structure beyond the important characteristics of branch ratio and molecular weight already noted.

Dimer and trimer fractions have been separated by distillation and components thereof further separated by gas chromatography. These lower oligomers and components along with complete reaction mixtures of HVI-PAO oligomers have been studied using infra-red spectroscopy and C-13 NMR. The studies have confirmed the highly uniform structural composition of the products of the invention, particularly when compared to conventional polyalphaolefins produced by $BF_3$, $AlCl_3$ or Ziegler-type catalysis. The unique capability of C-13 NMR to identify structural isomers has led to the identification of distinctive compounds in lower oligomeric fractions and served to confirm the more uniform isomeric mix present in higher molecular weight oligomers compatible with the finding of low branch ratios and superior viscosity indices.

1-Hexene HVI-PAO oligomers made by the present inventive process have been shown to have a very uniform linear $C_4$ branch and contain regular head-to-tail connections. In addition to the structures from the regular head-to-tail connections, the backbone structures have some head-to-head connection, indicative of the following structure as confirmed by NMR:

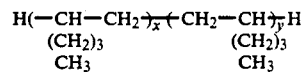

The oligomerization of 1-decene by reduced valence state, supported chromium also yields a HVI-PAO with a structure analogous to that of 1-hexene oligomer. The lubricant products after distillation to remove light fractions and hydrogenation have characteristic C-13 NMR spectra. In general, the novel oligomers have the following regular head-to-tail structure where n can be 3 to 17:

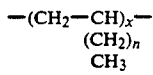

with some head-to-head connections.

The trimer of 1-decene HVI-PAO oligomer is separated from the oligomerization mixture by distillation from a 20 cS as-synthesized HVI-PAO in a short-path apparatus in the range of 165°–210° C. at 0.1–0.2 torr. The unhydrogenated trimer prepared in contact with hydrogen according to the process of this invention exhibited the following viscometric properties:

V @ 40° C., cS=14.88; V @ 100° C., cS=3.67;
VI=137

The trimer is hydrogenated at 235° C. and 4200 kPa $H_2$ with Ni on kieselguhr hydrogenation catalyst to give a hydrogenated HVI-PAO trimer with the following properties:

V @ 40° C., cS =16.66; V @ 100° C., cs =3.91;
VI=133;

Pour Point=less than −45° C.; Gas chromatographic analysis of the trimer reveals that it is composed of essentially two components having retention times of 1810 seconds and 1878 seconds under the following conditions: G. C. column-60 meter capillary column, 0.32 mmid, coated with stationary phase SPB-1 with film thickness 0.25 m, available from Supelco chromatography supplies, catalog no. 2-4046. Separation Conditions—Varian Gas chromatograph, model no. 3700, equipped with a flame ionization detector and capillary injector port with split ratio of about 50. $N_2$ carrier gas flow rate is 2.5 cc/minute. Injector port temperature 300° C.; detector port temperature 330° C., column temperature is set initially at 45° C. for 6 minutes, programmed heating at 15° C./minute to 300° C. final temperature and holding at final temperature for 60 minutes. Sample injection size is 1 microliter. Under these conditions, the retention time of a g.c. standard, n-dodecane, is 968 seconds.

The C-13 NMR spectra of the distilled C30 product confirms the chemical structures. The components are identified as 9-methyl, 11-octylheneicosane and 11-octyldocosane by infra-red and C-13 NMR analysis and are found to be present in a ratio between 1:10 and 10:1 heneicosane to docosane. The hydrogenated 1-decene trimer produced by the process of this invention has an index of refraction at 60° C. of 1.4396.

Olefins suitable for use as starting material in the invention include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic predominantly in the $C_6$–$C_{20}$ range, as for example 1-heptene to 1-hexadecene and more preferably $C_8$–$C_{14}$, 1-octene to 1-tetradecene, or mixtures of such olefins.

This class of alpha-olefin oligomers is prepared by oligomerization reactions in the presence of hydrogen in which a major proportion of the double bonds of the alphaolefins are not isomerized. These reactions include alphaolefin oligomerization by supported metal oxide catalysts, such as Cr compounds on silica or other supported IUPAC Periodic Table Group VIB compounds. The catalyst most preferred is a lower valence Group VIB metal oxide on an inert support. Although excellent catalytic properties are possessed by the lower valence state of Cr, especially CrII; conversion can be achieved to a lesser degree by reduced tungsten (W) and molybdenum (Mo) compounds. Preferred supports include silica, alumina, titania, silica alumina, magnesia and the like. The support material binds the metal oxide catalyst. Those porous substrates having a pore opening of at least 40 Angstroms are preferred.

The support material usually has high surface area and large pore volumes with average pore size of 40 to about 350 (A) angstroms. The high surface area are beneficial for supporting large amount of highly dispersive, active chromium metal centers and to give maximum efficiency of metal usage, resulting in very high activity catalyst. The support should have large average pore openings of at least 40 angstroms, with an average pore opening of 60 to 300 angstroms preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200 to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B$, $R_2Mg$, $RLi$, $R_2Zn$, where R is alkyl, alkoxy, aryl and the like. Preferred are CO or $H_2$ or metal alkyl containing compounds.

Alternatively, the Group VIB metal may be applied to the substrate in reduced form, such as CrII compounds. The resultant catalyst is very active for oligomerizing olefins at a temperature range of about 90°–250° C. (preferably 100°–180° C.) at autogenous pressure, or about 0.1 atmosphere to 5000 psi. Contact time can vary from one second to 24 hours; however, the weight hourly space velocity (WHSV) is really about 0.1 to 10 based on total catalyst weight. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged at successively higher temperatures to about 600° for a period of about 16 to 20 hours. Thereafter the catalyst is cooled down under an inert atmosphere to a temperature of about 250 to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have a very wide range of viscosities with high viscosity indices suitable for high performance lubrication use. The product oligomers also have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices. These low branch oligomers maintain better or comparable pour points.

The branch ratios defined as the ratios of $CH_3$ groups to $CH_2$ groups in the lube oil are calculated from the weight fractions of methyl groups obtained by infrared methods, published in *Analytical Chemistry*, Vol. 25, No. 10, p. 1466 (1953).

$$\text{Branch ratio} = \frac{\text{wt fraction of methyl group}}{1 - (\text{wt fraction of methyl group})}$$

As referenced hereinbefore, supported Cr metal oxide in different oxidation states is known to polymerize alpha olefins from $C_3$ to $C_{20}$ (De 3427319 to H. L. Krauss and Journal of Catalysis 88, 424–430, 1984) using a catalyst prepared by $CrO_3$ on silica. The referenced disclosures teach that polymerization takes place at low temperature, usually less than 100° C., to give adhesive polymers and that at high temperature, the catalyst promotes isomerization, cracking and hydrogen transfer reactions. The present inventions produce low molecular weight oligomeric products in the presebce of hydrogen under reaction conditions and using catalysts which minimize side reactions such as 1-olefin isomerization, cracking, hydrogen transfer and aromatization. To produce molecular weight products suitable for use as lube basestock or as blending stock with other lube stock, the reaction of the present invention is carried out at a temperature higher (90°–250° C.) than the temperature suitable to produce high molecular weight polyalpha-olefins. The preferred conditions for reaction is the temperature range of 100°–200° C. an autogenous pressure. The standard synthesis process uses a controlled optimum reaction temperature of about 125° C. The catalysts used in the present invention do not cause a significant amount of side reactions even at high temperature when oligomeric, low molecular weight fluids are produced.

The catalysts for this invention thus minimize all side reactions but oligomerize alpha olefins in the presence of hydrogen to give low molecular weight polymers with high efficiency. It is well known in the prior art that chromium oxides, especially chromia (III) with average +3 oxidation states, either pure or supported, catalyze double bond isomerization, dehydrogenation, cracking, etc. Although the exact nature of the supported Cr oxide is difficult to determine, it is thought that the catalyst of the present invention is rich in Cr (II) supported on silica, which is more active to catalyze alpha-olefin oligomerization at high reaction temperature without causing significant amounts of isomerization, cracking or hydrogenation reactions, etc. However, catalysts as prepared in the cited references can be richer in Cr (III). They catalyze alpha-olefin polymerization at low reaction temperature to produce high molecular weight polymers. However, as the references teach, undesirable isomerization, cracking and hydrogenation reaction takes place at higher temperatures needed to produce lubricant products. The prior art also teaches that supported Cr catalysts rich in Cr(III) or higher oxidation states catalyze 1-butene isomerization with $10^3$ higher activity than polymerization of 1-butene. The quality of the catalyst, method of preparation, treatments and reaction conditions are critical to the catalyst performance and composition of the product produced and distinguish the present invention over the prior art. In the instant invention very low catalyst concentrations based on feed, from 10 wt % to 0.01 wt %, are used to produce oligomers; whereas, in the cited references catalyst ratios based on feed of 1:1 are used to prepare high polymer. Resorting to lower catalyst concentrations in the present invention to produce lower molecular weight material runs counter to conventional polymerization theory, compared to the results in the cited references.

The oligomers of 1-olefins prepared in this invention usually have much lower molecular weights than the polymers produced in cited reference which are semisolids, with very high molecular weights. They are not suitable as lubricant basestocks. These high polymers usually have not detectable amount of monomer, dimer or trimmer ($C_{10}$–$C_{30}$) components from synthesis. These high polymers also have very low unsaturation content. However, products in this invention are free-flowing liquids at room temperature, suitable for lube basestock, and may contain significant amount of dimer or trimer and have high unsaturations.

The following examples are presented to illustrated the method of catalyst preparation used in this invention and the oligomerization reaction conducted both without added hydrogen and with added hygrogen according to the instant imvention. The Examples are presented merely for illustration purposes and are not intended to limit the scope of the present invention.

EXAMPLE 1

Catalyst Preparation and Activation Procedure 1.9 grams of chromium (II) acetate $(Cr_2(OCOCH_3)_4 2H_2O)$ (5.58 mmole) (commercially obtained) is dissolved in 50 cc of hot acetic acid. Then 50 grams of a silica gel of 8–12 mesh size, a surface area of 300 m²/g, and a pore volume of 1 cc/g, also is added. Most of the solution is absorbed by the silica gel. The final mixture is mixed for half an hour on a rotavap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$ and ready for use.

EXAMPLE 2

The catalyst prepared in Example 1 (3.2 g ) is packed in a ⅜" stainless steel tubular reactor inside an $N_2$ blanketed dry box. The reactor under $N_2$ atmosphere is then heated to 150° C. by a single-zone Lindberg furnace. Pre-purified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt % | 10 | 41 | 74 | 31 |
| Viscosity, cS, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

EXAMPLE 3

Similar to Example 2, a fresh catalyst sample is charged into the reactor and 1-hexene is pumped to the reactor at 1 atm and 10 cc per hour. As shown below, a lube of high viscosities and high VI's is obtained. These runs show that at different reaction conditions, a lube product of high viscosities can be obtained.

| Sample | A | B |
|---|---|---|
| T.O.S., hrs. | 20 | 44 |
| Temp., °C. | 100 | 50 |
| Lube Yield, % | 8.2 | 8.0 |
| Viscosities, cS at | | |
| 40° C. | 13170 | 19011 |
| 100° C. | 620 | 1048 |
| VI | 217 | 263 |

EXAMPLE 4

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
|---|---|---|---|---|
| T.O.S., hrs. | 3.5 | 4.5 | 6.5 | 22.5 |
| Lube Yield, % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

These runs show that different Cr on a silica catalyst are also effective for oligomerizing olefins to lube products.

EXAMPLE 5

As in Example 4, purified 1-decene is pumped through the reactor at 250 to 320 psi. The product is collected periodically and stripped of light products boiling points below 650° F. High quality lubes with high VI are obtained (see following table).

| Reaction Temp. °C. | WHSV g/g/hr | Lube Product Properties | | |
|---|---|---|---|---|
| | | V at 40° C. | V at 100° C. | VI |
| 120 | 2.5 | 1555.4 cs | 157.6 cs | 217 |
| 135 | 0.6 | 389.4 | 53.0 | 202 |
| 150 | 1.2 | 266.8 | 36.2 | 185 |
| 166 | 0.6 | 67.7 | 12.3 | 181 |
| 197 | 0.5 | 21.6 | 5.1 | 172 |

EXAMPLE 6

Similar catalyst is used in testing 1-hexene oligomerization at different temperature. 1-Hexene is fed at 28 cc/hr and at 1 atmosphere.

| Sample | G | H |
|---|---|---|
| Temperature, °C. | 110 | 200 |
| Lube Yield, wt. % | 46 | 3 |
| Viscosities, cS at | | |
| 40° C. | 3512 | 3760 |
| 100° C. | 206 | 47 |
| VI | 174 | 185 |

EXAMPLE 7

1.5 grams of a similar catalyst as prepared in Example 4 was added to a two-neck flask under $N_2$ atmosphere. Then 25 g of 1-hexene was added. The slurry was heated to 55° C. under $N_2$ atmosphere for 2 hours. Then some heptane solvent was added and the catalyst was removed by filtration. The solvent and unreacted starting material was stripped off to give a viscous liquid with a 61% yield. This viscous liquid had viscosities of 1536 and 51821 cS at 100° C. and 40° C., respectively. This example demonstrated that the reaction can be carried out in a batch operation.

The 1-decene oligomers as described below were synthesized by reacting purified 1-decene with an activated chromium on silica catalyst. The activated catalyst was prepared by calcining chromium acetate (1 or 3% Cr) on silica gel at 500°-800° C. for 16 hours, followed by treating the catalyst with CO at 300°-350° C. for 1 hour. 1-Decene was mixed with the activated catalyst and heated to reaction temperature for 16-21 hours. The catalyst was then removed and the viscous product was distilled to remove low boiling components at 200° C./0.1 mm Hg.

Reaction conditions and results for the lube synthesis of HVI-PAO are summarized below:

TABLE 1

| Example No. | Cr on Silica | Calcination Temp. | Treatment Temp. | 1-decene/Catalyst Ratio | Lube Yld |
|---|---|---|---|---|---|
| 8 | 3 wt % | 700° C. | 350° C. | 40 | 90 |
| 9 | 3 | 700 | 350 | 40 | 90 |
| 10 | 1 | 500 | 350 | 45 | 86 |
| 11 | 1 | 600 | 350 | 16 | 92 |

TABLE 2

| | Branch Ratios and Lube Properties of Examples 8-11 Alpha Olefin Oligomers | | | |
|---|---|---|---|---|
| Example No. | Branch $CH_3$ Ratios $CH_2$ | $V_{40°}$ C. cS | $V_{100°}$ C. cS | VI |
| 8 | 0.14 | 150.5 | 22.8 | 181 |
| 9 | 0.15 | 301.4 | 40.1 | 186 |
| 10 | 0.16 | 1205.9 | 128.3 | 212 |

TABLE 2-continued

Branch Ratios and Lube Properties of
Examples 8-11 Alpha Olefin Oligomers

| Example No. | Branch $CH_3$ Ratios $CH_2$ | $V_{40}°$ C. cS | $V_{100}°$ C. cS | VI |
|---|---|---|---|---|
| 11 | 0.15 | 5238.0 | 483.1 | 271 |

EXAMPLE 12

A commercial Cr on silica catalyst which contains 1% Cr on a large pore volume synthetic silica gel is used. The catalyst is first calcined with air at 700° C. for 16 hours and reduced with CO at 350° C. for one to two hours. 1.0 part by weight of the activated catalyst is added to 1-decene of 200 parts by weight in a suitable reactor and heated to 185° C. 1-Decene is continuously fed to the reactor at 2-3.5 parts/minute and 0.5 parts by weight of catalyst is added for every 100 parts of 1-decene feed. After 1200 parts of 1-decene and 6 parts of catalyst are charged, the slurry is stirred for 8 hours. The catalyst is filtered and light product boiled below 150° C. @ 0.1 mm Hg is stripped. The residual product is hydrogenated with a Ni on Kieselguhr catalyst at 200° C. The finished product has a viscosity at 100° C. of 18.5 cs, VI of 165 and pour point of −55° C.

EXAMPLE 13

Similar as in Example 12, except reaction temperature is 125° C. The finished product has a viscosity at 100° C. of 145 cs, VI of 214, pour point of −40° C.

EXAMPLE 14

Similar as in Example 12, except reaction temperature is 100° C. The finished product has a viscosity at 100° C. of 298 cs, VI of 246 and pour point of −32° C.

The final lube products in Example 12 to 14 contain the following amounts of dimer and trimer and isomeric distribution (distr.).

| | Example | | |
|---|---|---|---|
| | 16 | 13 | 14 |
| V @ 100° C., cS | 18.5 | 145 | 298 |
| VI | 165 | 214 | 246 |
| Pour Point,°C. | −55° C. | −40° C. | −32 |
| wt % dimer | 0.01 | 0.01 | 0.027 |
| wt % isomeric distr. dimer | | | |
| n-eicosane | 51% | 28% | 73% |
| 9-methylnonacosane | 49% | 72% | 27% |
| wt % trimer | 5.53 | 0.79 | 0.27 |
| wt % isomeric distr. trimer | | | |
| 11-octyldocosane | 55 | 48 | 44 |
| 9-methyl,11-octyl-heneicosane | 35 | 49 | 40 |
| others | 10 | 13 | 16 |

These three examples demonstrate that HVI-PAO of wide viscosities contain the dimer and trimer of unique structures in various proportions. The molecular weights and molecular weight distributions are analyzed by a high pressure liquid chromatography, composed of a Constametric II high pressure, dual piston pump from Milton Roy Co. and a Tracor 945 LC detector. During analysis, the system pressure is 650 psi and THF solvent (HPLC grade) deliver rate is 1 cc per minute. The detector block temperature is set at 145° C. 50 microliter of sample, prepared by dissolving 1 gram PAO sample in 100 cc THF solvent, is injected into the chromatograph. The sample is eluted over the following columns in series, all from Waters Associates: Utrastyragel $10^5$ A, P/N 10574, Utrastyragel $10^4$ A, P/N 10573, Utrastyragel $10^3$ A, P/N 10572, Utrastyragel 500 A, P/N 10571. The molecular weights are calibrated against commercially available PAO from Mobil Chemical Co, Mobil SHF-61 and SHF-81 and SHF-401.

The following table summarizes the molecular weights and distributions of Examples 12 to 14.

| | Examples | | |
|---|---|---|---|
| | 16 | 13 | 14 |
| V @ 100°C., cs | 18.5 | 145 | 298 |
| VI | 165 | 214 | 246 |
| number-averaged molecular weights, $MW_n$ | 1670 | 2062 | 5990 |
| weight-averaged molecular weights, $MW_w$ | 2420 | 4411 | 13290 |
| molecular weight distribution, MWD | 1.45 | 2.14 | 2.22 |

Under similar conditions, HVI-PAO product with viscosity as low as 3 cs and as high as 500 cs, with VI between 130 and 280, can be produced.

As illustrated above, low viscosity HVI-PAO can be produced from 1-alkenes reaction over activated chromium on $SiO_2$ catalyst at high reaction temperature. However, carrying out these oligomerizations at high temperature leads to undesirable side reactions, including isomerization and accelerated catalyst aging. Consequently, lube yields are decreased and catalyst productivity is lowered. Now it has been found that the addition or cofeeding of a small amount of hydrogen during 1-alkene oligomerization over activated chromium on $SiO_2$ reduces product molecular weight or viscosity. Accordingly, the addition of hydrogen during oligomerization allows a lower viscosity product to be produced at a lower temperature with a minimum of side rections and catalyst aging.

Surprisingly, the addition of hydrogen to the oligomerization reaction does not result in hydrogenation of the starting olefins in the oligomeriztion reaction or in hydrogenation of the product polyalpha-olefin HVI-PAO lube. The product HVI-PAO can be separated as an unsaturated product and further hydrogenated to give lube stocks with high VI.

In Examples 15-20 the oligomerization reaction is carried out both without hydrogen and in contact with hydrogen to illustrate the discovery of the present invention.

EXAMPLES 15-20

The same catalyst is used throughout the runs and is prepared initially as described above by calcination of chromiun oxide on silica with air at 700° C., followed by reduction at 350° C. with CO. For Examples 15-20 the catalyst is regenerated by calcination at 500° C. with air and reduction at 350° C. with CO. Three grams of the catalyst is packed in a ⅜" id stainless steel reactor and heated to reaction temperature. The reaction conditions and product properties are shown in the following Table 3.

TABLE

| Ex. No. | Time, hrs. | Temp °C. | H₂ feed cc/min. | Lube yld. wt % | Lube Properties | | |
|---|---|---|---|---|---|---|---|
| | | | | | V @ 40° C., cS | V @ 100° C., cs | VI |
| 15 | 0–68 | 147 | 0 | 89 | 366.0 | 47.7 | 191 |
| 16 | 68–140 | 147 | 0 | 87 | 381.7 | 49.1 | 191 |
| 17 | 140–164 | 147 | 0 | 80 | 480.3 | 57.5 | 189 |
| 18 | 164–212 | 147 | 7 | 54 | 155.8 | 23.5 | 185 |
| 19 | 212–260 | 147 | 3 | 73 | 358.1 | 45.7 | 187 |
| 20 | 260–382 | 171 | 0 | 57 | 123.3 | 19.2 | 176 |

In Example 18 the molar ratio of 1-decene to hydrogen is 3. In Example 19 the molar ratio of 1-decene to hydrogen is 6. However, the molar ratio of 1-alkene to hydrogen can be between 0.1 and 50, with a preferred ratio of 1 to 10.

From the foregoing Examples 15–20 it is evident that the addition of hydrogen in the oligomerization step results in a reduction of product viscosity at the same reaction temperature. The product viscosity of Example 17, for instance, was reduced from 57.5 cS to 23.5 cS in Example 18 upon the addition of H₂ to the reaction. Similarly, when H₂ was cofed as in Example 19 the product viscosity was 45.7 cS.

The use of reduced chromium oxide catalyst to oligomerize olefins to produce low branch ratio lube products with low pour points was heretofore unknown. Catalytic production of oligomers with structures having a low branch ratio which does not use a corrosive co-catalyst and produces a lube with a wide range of viscosities and good V.I.'s was also heretofore unknown and more specifically the preparation of lube oils having a branch ratio of less than about 0.19 was also unknown heretofore.

While the invention has been described with preferred embodiments, the inventive concept is not limited except as set forth in the following claims.

What is claimed is:

1. A process for the preparation of liquid hydrocarbons suitable as lubricant basestocks from alpha-olefins containing 6 to 20 carbon atoms, or mixtures of such olefins, comprising: contacting a feedstream comprising said olefins and hydrogen under oligomerization conditions, at reaction temperature of about 90 to 250° C. with a chromium catalyst on a porous support, which catalyst has been treated by oxidation at a temperature of 200° C. to 900° C. in the presence of an oxidizing gas and then by treatment with a reducing agent at a temperature and for a time sufficient to reduce said catalyst to a lower valence state; whereby an oligomeric liquid lubricant composition comprising $C_{30}$–$C_{1300}$ hydrocarbons is obtained, said composition having a branch ratio of less than 0.19, weight average molecular weight between 420 and 45,000, number average molecular weight between 420 and 18,000, molecular weight distribution between 1 and 5 and pour point below −15° C.

2. The process of claim 1 wherein the liquid lubricant composition has a viscosity index greater than 130.

3. The process of claim 1 wherein the liquid lubricant composition has a $C_{30}$ fraction with a branch ratio below 0.19, viscosity index greater than 130 and pour point below −45° C.

4. The process of claim 1 wherein said reducing agent comprises CO, the oligomerization temperature is about 100°–180° C., and the yield of $C_{30+}$ oligomer is at least 85 wt % for product having a viscosity of at least 15 cS at 100° C.

5. The process of claim 4 wherein the support comprises porous silica.

6. The process of claim 4 wherein the olefin consists essentially of 1-octene, 1-decene, 1-dodecene, 1-tetradecene or mixtures thereof.

7. The process of claim 4 wherein the olefin consists essentially of 1-decene.

8. The process of claim 1 wherein said catalyst is not subjected to a further oxidation step after said reduction.

9. The process of claim 1 wherein said olefin comprises 1-decene, and the oligomer has a VI of 181 or greater and a branch ratio of from about 0.14 to 0.16.

10. A process for oligomerizing alpha-olefin to produce lubricant range hydrocarbon stock including the step of contacting said alpha-olefin and hydrogen with a supported solid reduced metal oxide catalyst under oligomerization conditions at a temperature of about 90 to 250° C.; said metal oxide comprising a lower valence form of at least one Group VIB metal, whereby the lubricant range hydrocarbon product has a branch ratio from about 0.10 to about 0.16 and a viscosity index of at least about 130.

11. The process of claim 10 wherein said alpha olefin comprises olefinic hydrocarbon having 8 to 14 carbon atoms or mixtures thereof; wherein the process conditions include reaction temperature of about 90° C. to 200° C.; and wherein said support catalyst includes a porous inert support having a pore opening of at least 40 Angstroms.

12. The process of claim 11 wherein the process conditions are controlled to oligomerize alpha olefin without isomerizing double bonds therein.

13. The process of claim 11 wherein said catalyst comprises chromium oxide prepared by treating an oxidized chromium oxide with a reducing agent for a time sufficient to reduce said chromium oxide.

14. A process for oligomerizing alpha olefin to produce lubricant range hydrocarbon including the step of contacting a feedstream comprising $C_6$–$C_{20}$ alpha olefin and hydrogen with a supported solid reduced metal oxide catalyst under oligomerization conditions at a temperature of about 90 to 250° C.; said metal oxide comprising a lower valence form of at least one Group VIB metal to produce lubricant range hydrocarbon product having a branch ratio from about 0.10 to about 0.16 and a viscosity index of at least about 130.

15. The process of claim 14 wherein the hydrocarbon product has a pour point less than −15° C.

16. The process of claim 14 wherein hydrocarbon product contains 9-methyl,11-octylheneicosane and 11-octyldocosane in a mole ratio of 1:10 to 10:1.

17. The process of claim 16 wherein said mole ratio is about 1:2 to 2:1.

18. A process for oligomerizing alpha olefin to produce lubricant range hydrocarbon stock including the step of contacting a feedstream comprising said alpha olefin and hydrogen with a supported solid reduced chromium catalyst under oligomerization conditions at a temperature of about 90 to 250° C. to produce liquid lubricant hydrocarbon comprising the polymeric residue of l-alkenes consisting essentially of linear $C_6$-$C_{20}$ l-alkenes, said composition having a branch ratio of less than 0.19, weight average molecular weight between 420 and 45,000, number average molecular weight between 420 and 18,000, molecular weight distribution between 1 and 5 and pour point below $-15°$ C.; and wherein the lubricant range hydrocarbon product has viscosity index of about 130 to 280 and viscosity up to about 750 cS.

19. The process of claim 18 wherein said alpha olefin consists essentially of hydrocarbon having 8 to 14 carbon atoms or mixtures thereof; wherein the process conditions include reaction temperature of about 90° C. to 180° C.; and wherein said support catalyst includes a porous inert support.

20. The process of claim 18 wherein the oligomerization conditions comprise reaction temperature of about 90°-250° C. and feedstock to catalyst weight ratio between 10:1 and 30:1; said catalyst comprises CO reduced $CrO_3$ and said support comprises silica having a pore size of at least 40 Angstroms.

21. The process of claim 1 wherein the molar ratio of said alpha olefin to said hydrogen is between 0.1 and 50.

22. The process of claim 1 wherein the molar ratio of said alpha olefin to said hydrogen is preferably about 1 to 10.

23. A process for controlling product viscosity in the oligomerization of alpha-olefin to produce reduced viscosity lubricant range hydrocarbon, comprising;
cofeeding $C_6$-$C_{20}$ alpha-olefins and hydrogen to an oligomerization zone under oligomerization conditions, at reaction temperature of about 90 to 250° C. with a chromium catalyst on a porous support, which catalyst has been treated by oxidation at a temperature of 200° C. to 900° C. in the presence of an oxidizing gas and then by treatment with a reducing agent at a temperature and for a time sufficient to reduce said catalyst to a lower valence state; whereby an oligomeric liquid lubricant composition comprising $C_{30}$-$C_{1300}$ hydrocarbons of lower viscosity is obtained, said composition having a branch ratio of less than 0.19, weight average molecular weight between 420 and 45,000, number average molecular weight between 420 and 18,000, molecular weight distribution between 1 and 5 and pour point below $-15°$ C.

24. The process of claim 23 wherein the molar ratio of said alpha olefin to said hydrogen is between 0.1 and 50.

25. The process of claim 23 wherein the molar ratio of said alpha olefin to said hydrogen is preferably about 1 to 10.

* * * * *